United States Patent
Hettrick et al.

(10) Patent No.: US 8,938,292 B2
(45) Date of Patent: Jan. 20, 2015

(54) ESTIMATING CARDIOVASCULAR PRESSURE AND VOLUME USING IMPEDANCE MEASUREMENTS

(75) Inventors: Douglas A. Hettrick, Andover, MN (US); Yong K. Cho, Maple Grove, MN (US); Mattias Rouw, Arnhem (NL); Shantanu Sarkar, Roseville, MN (US); Todd M. Zielinski, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 1309 days.

(21) Appl. No.: 12/263,065

(22) Filed: Oct. 31, 2008

(65) Prior Publication Data

US 2010/0030087 A1  Feb. 4, 2010

Related U.S. Application Data

(60) Provisional application No. 61/085,235, filed on Jul. 31, 2008.

(51) Int. Cl.
*A61B 5/05* (2006.01)
*A61N 1/365* (2006.01)
(Continued)

(52) U.S. Cl.
CPC .......... *A61N 1/36521* (2013.01); *A61B 5/0215* (2013.01); *A61B 5/0535* (2013.01);
(Continued)

(58) Field of Classification Search
USPC ......... 600/300, 301, 481, 485, 486, 504, 506, 600/507, 547, 561; 128/898
See application file for complete search history.

(56) References Cited

U.S. PATENT DOCUMENTS

| | | |
|---|---|---|
| 4,374,382 A | 2/1983 | Markowitz |
| 4,674,518 A | 6/1987 | Salo |

(Continued)

FOREIGN PATENT DOCUMENTS

| | | |
|---|---|---|
| WO | WO 2005/110535 A1 | 11/2005 |
| WO | WO2005110535 A1 | 11/2005 |

(Continued)

OTHER PUBLICATIONS

Klotz et al., Single-beat estimation of end-diastolic pressure-volume relationship: a novel method with potential for noninvasive application, 2006, Am J Physiol Heart Circ Physiol, vol. 291, pp. H403-H412.*

(Continued)

*Primary Examiner* — Melanie Y Brown
*Assistant Examiner* — Erik B Crawford
(74) *Attorney, Agent, or Firm* — Michael C. Soldner

(57) ABSTRACT

Techniques for estimating a cardiac chamber or vascular pressure based upon impedance are described. A device or system may measure an impedance between at least two electrodes implanted within or proximate to a cardiovascular system. The device or system may estimate a pressure of an element of the cardiovascular system based on a relationship between impedance and volume of the element, and based on a empirical relationship between the volume and the pressure. The device or system may also estimate the dimension of the element based on the impedance-volume relationship, or other characteristics based on the impedance. Because the impedance measurements may be obtained, in some examples, by using electrodes and leads implanted within the cardiovascular system and coupled to an implantable medical device, a practical estimation of a cardiovascular pressure can be obtained on a chronic basis without requiring the use other invasive sensors, such as micronanometer transducers.

41 Claims, 10 Drawing Sheets

(51) Int. Cl.
*A61B 5/0215* (2006.01)
*A61B 5/053* (2006.01)
*A61B 5/021* (2006.01)
*A61B 5/00* (2006.01)

(52) U.S. Cl.
CPC .............. *A61B5/0538* (2013.01); *A61B 5/021* (2013.01); *A61B 5/02158* (2013.01); *A61B 5/053* (2013.01); *A61N 1/36564* (2013.01); *A61B 5/7239* (2013.01)
USPC ........... 600/547; 128/898; 600/300; 600/301; 600/481; 600/485; 600/504; 600/506; 600/507; 600/561

(56) References Cited

U.S. PATENT DOCUMENTS

| | | | |
|---|---|---|---|
| 4,807,638 | A | 2/1989 | Sramek |
| 5,003,976 | A | 4/1991 | Alt |
| 5,117,824 | A | 6/1992 | Keimel et al. |
| 5,417,717 | A | 5/1995 | Salo et al. |
| 5,824,029 | A | 10/1998 | Weijand et al. |
| 6,360,123 | B1 | 3/2002 | Kimchi et al. |
| 6,438,408 | B1 | 8/2002 | Mulligan et al. |
| 6,623,434 | B2 | 9/2003 | Chesney et al. |
| 6,648,828 | B2 | 11/2003 | Friedman et al. |
| 6,871,089 | B2 | 3/2005 | Korzinov et al. |
| 7,029,447 | B2 | 4/2006 | Rantala |
| 7,164,947 | B2 | 1/2007 | Holmstrom et al. |
| 7,181,272 | B2 | 2/2007 | Struble et al. |
| 7,283,873 | B1 | 10/2007 | Park et al. |
| 7,391,257 | B1 | 6/2008 | Denison et al. |
| 7,736,319 | B2 | 6/2010 | Patangay et al. |
| 2004/0147969 | A1 | 7/2004 | Mann et al. |
| 2005/0096557 | A1 | 5/2005 | Vosburgh et al. |
| 2005/0159639 | A1* | 7/2005 | Skliar et al. ..................... 600/16 |
| 2005/0192488 | A1 | 9/2005 | Bryenton et al. |
| 2006/0074404 | A1 | 4/2006 | Struble |
| 2007/0021683 | A1 | 1/2007 | Benditt et al. |
| 2007/0129765 | A1 | 6/2007 | Gilkerson et al. |
| 2008/0033498 | A1 | 2/2008 | Mann et al. |
| 2008/0103399 | A1 | 5/2008 | Patangay et al. |
| 2008/0132800 | A1 | 6/2008 | Hettrick et al. |
| 2009/0275854 | A1* | 11/2009 | Zielinski et al. .............. 600/547 |
| 2010/0113945 | A1* | 5/2010 | Ryan ........................... 600/486 |
| 2010/0274306 | A1* | 10/2010 | Pastore et al. ..................... 607/3 |

FOREIGN PATENT DOCUMENTS

| | | |
|---|---|---|
| WO | WO 2006/102905 A1 | 10/2006 |
| WO | 2008082802 | 7/2008 |

OTHER PUBLICATIONS

International Search Report and Written Opinion of corresponding PCT Application No. PCT/US2009/052450 dated Oct. 30, 2009 (14 pages).

Office Action from U.S. Appl. No. 12/262,941 dated Oct. 18, 2011 (15 pages).

Response to Office Action from U.S. Appl. No. 12/262,941 dated Oct. 18, 2011 filed on Jan. 18, 2012 (11 pages).

Paul Steendijk et al., "Pressure-volume measurements by conductance catheter during cardiac resynchronization therapy," *European Heart Journal Supplements* (2004) 6 (Supplement D), D35-D42.

A.V. Blinov et al., "Plethysmographic Impedance Device for Measuring Blood Pressure," *Measurement Technniques*, vol. 40, No. 2, 1997 (pp. 188-192).

Klaas R. Visser et al., "Blood Pressure Esimation Investigated by Electric Impedance Measurement," *Annual International Conference of the IEEE Engineering in Medicine and Biology Society*, vol. 12, No. 2 (1990) pp. 691-692.

U.S. Appl. No. 12/262,941, filed Oct. 31, 2008 entitled Monitoring Hemodynamic Status Based on Intracardiac or Vascular Impedance by Todd M. Zielinski et al.

Notice of Allowance from U.S. Appl. No. dated May 1, 2012 (10 pages).

\* cited by examiner

ESTIMATING CARDIOVASCULAR PRESSURE AND VOLUME USING IMPEDANCE MEASUREMENTS

This application claims the benefit of U.S. Provisional Application No. 61/085,235, filed Jul. 31, 2008, which is hereby incorporated by reference in its entirety.

TECHNICAL FIELD

The disclosure relates to implantable medical devices, and, more particularly, to implantable medical devices that monitor cardiovascular pressure or volume.

BACKGROUND

Congestive Heart Failure (CHF) refers to a clinical syndrome of symptomatic events associated with compromised cardiac function. The term "heart failure" may describe the inability of the heart to supply sufficient blood flow to meet the physiological needs of the peripheral tissues. Heart failure may be associated with either systolic dysfunction or diastolic dysfunction. In some cases, both systolic and diastolic dysfunction may coexist.

Systolic dysfunction refers to the inability of the cardiac contractile mechanism to develop adequate force, e.g., the inability to overcome mechanical afterload. The heart may compensate for reduced systolic dysfunction by dilating or stretching in order to improve ejection by increasing preload via the Frank-Starling mechanism. Thus, systolic dysfunction may often be characterized by a dilated, thin-walled ventricle with low ejection fraction.

Diastolic dysfunction refers to the inability of a ventricle to adequately fill. Diastolic dysfunction may arise from several mechanisms, including hypertension. Increased afterload due to increased systemic vascular resistance or reduced arterial compliance can lead to increased wall stress according to the Law of LaPlace. The ventricle may compensate for such increased wall stress by thickening or hypertrophying. Thus, diastolic ventricular dysfunction may often be characterized by ventricular hypertrophy and perhaps increased ejection fraction.

The myocardium may be thought of as a viscoelastic material with time-varying mechanical properties that rhythmically contracts against an incompressible fluid (blood), itself contained in viscoelastic network of blood vessels. Ventricular "preload" describes the stretch on the myocardial fibers just prior to contraction. Preload may be estimated clinically as left ventricular end diastolic volume (LVEDV).

Both systolic and diastolic dysfunction can lead to symptoms of CHF. Both may also be associated with increased ventricular filling pressures and volumes. However, systolic dysfunction may be closely associated with left ventricle (LV) dilation (i.e., increased preload), while diastolic dysfunction may be associated with reduced LV end diastolic volume.

Proposed techniques to estimate cardiac chamber or vascular pressure rely on invasive placement of high fidelity micronanometer transducers directly into the chamber of interest including the ventricles, atria or great vessels. It has been proposed to incorporate such transducers onto standard implantable pacemaker or pacemaker-cardioverter-defibrillator leads or lead configurations. This may increase the size of the lead, or may require the placement of one or more additional leads (compared to a standard device implant) for pressure monitoring. Measurements of cardiac chamber dimension typically require acute invasive or non-invasive test equipment such as ventriculography, echocardiography, or magnetic resonance imaging.

SUMMARY

In general, this disclosure is directed to techniques for estimating a cardiovascular pressure and/or a cardiovascular volume based upon a measured impedance. The estimated pressure or volume may be estimated for a cardiac chamber, blood vessel, or other cardiovascular component, e.g., the aorta or the vena cava. In some examples, these estimates may be made by or using an implantable medical device (IMD) coupled to intracardiac leads in a typical configuration for sensing, pacing and, in some cases, delivery of therapeutic shocks.

To facilitate the estimation techniques, a first relationship between volume and pressure may be determined for a cardiac chamber or for a vascular lumen. The first relationship may be based upon empirical data. In addition, a second relationship between impedance and volume may be determined based upon empirical data, electrode positioning data, and/or blood resistance data.

An IMD or other device may use the first relationship in conjunction with the second relationship in order to estimate cardiac chamber or vascular pressure. In some examples, the first and second relationships may be combined into a composite relationship for estimating cardiovascular pressure based on measured impedance. In some examples, the second relationship may be used to estimate chamber or vascular volume, i.e., dimension, based on impedance.

The impedance may be measured using at least two electrodes implanted within or proximate to a cardiovascular system. In some examples, the electrodes may be stimulation and/or sensing electrodes typically coupled to an IMD for cardiac sensing, pacing, and/or delivery of therapeutic shocks. Because the impedance measurements may be obtained by using such electrodes, a practical estimation of cardiac pressure and vascular pressure can be obtained without requiring the use other invasive sensors, such as micronanometer transducers.

In one example, a method includes measuring an impedance between at least two electrodes implanted within a cardiovascular system. The method further includes estimating a pressure of an element of the cardiovascular system based on a relationship between the measured impedance and a volume of the element of the cardiovascular system and based on a relationship between the volume and the pressure.

In another example, an implantable medical device includes an impedance measurement block configured to measure an impedance between at least two electrodes implanted within the cardiovascular system. The device further includes a memory configured to store a relationship between an impedance and a volume of an element of the cardiovascular system, and to store a relationship between the volume and a pressure of the element of the cardiovascular system. The device further includes a processor configured to estimate a pressure of an element of the cardiovascular system based on a relationship between the measured impedance and a volume of the element of the cardiovascular system and based on a relationship between the volume and the pressure.

In another example, a system includes a means for measuring an impedance between at least two electrodes implanted within a cardiovascular system. The system further includes a means for estimating a pressure of an element of the cardiovascular system based on a relationship between the measured impedance and a volume of the element of the cardiovascular system and based on a relationship between the volume and the pressure.

The techniques described in this disclosure may be implemented in hardware, software, firmware, or a combination thereof. If implemented in software, the software may be executed by one or more processors. The software may be initially stored in a computer readable medium and loaded by a processor for execution. Accordingly, this disclosure contemplates computer-readable media comprising instructions to cause one or more processors to perform techniques as described in this disclosure.

For example, in some aspects, the disclosure provides a computer-readable medium comprising instructions that when executed cause a processor to measure an impedance between at least two electrodes implanted within a cardiovascular system. The computer-readable medium also comprises instructions that when executed cause a processor to estimate a pressure of an element of the cardiovascular system based on a relationship between the measured impedance and a volume of the element of the cardiovascular system and based on a relationship between the volume and the pressure.

The details of one or more examples of the invention are set forth in the accompanying drawings and the description below. Other features, objects, and advantages of the invention will be apparent from the description and drawings, and from the claims.

DETAILED DESCRIPTION

Figure 1:
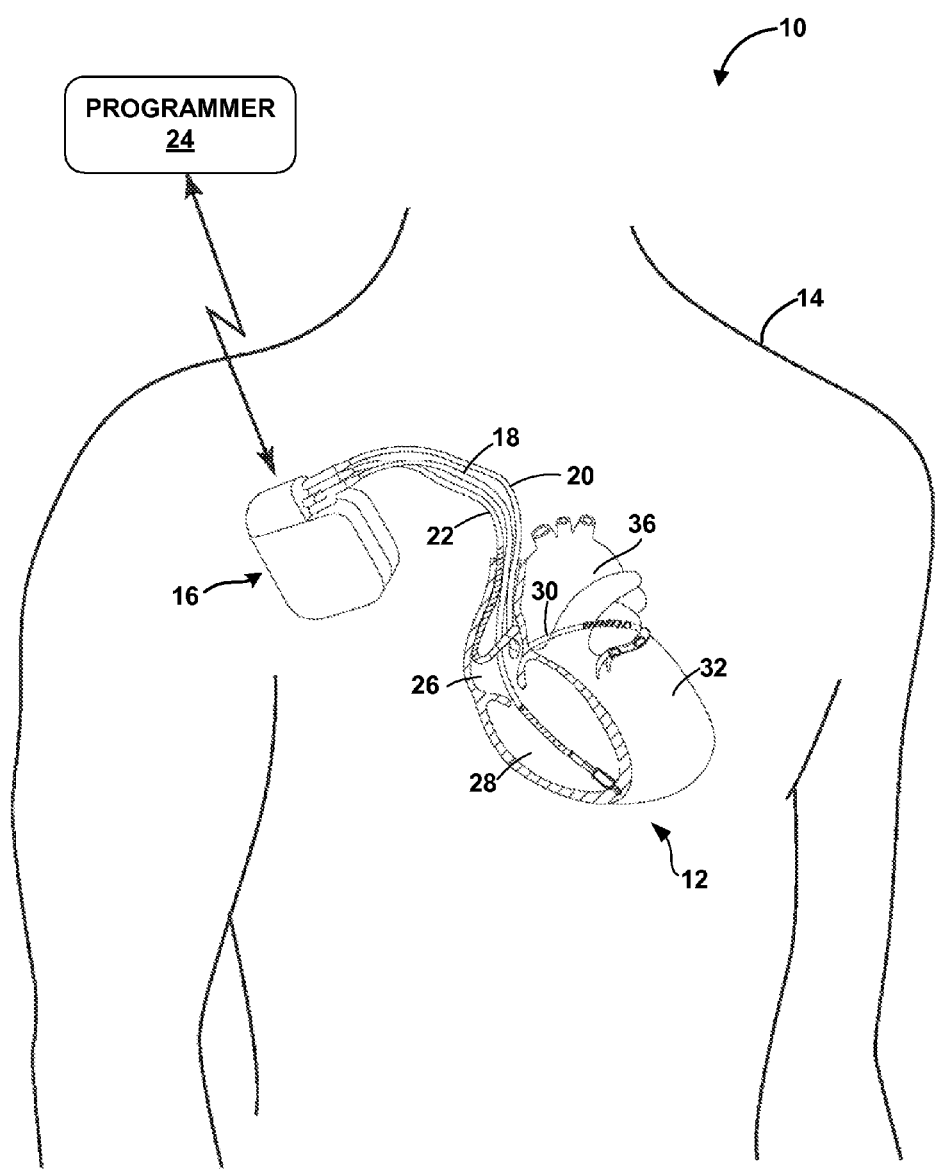
FIG. 1 is a conceptual diagram illustrating an example therapy system comprising an implantable medical device (IMD) that may be used to monitor one or more physiological parameters of a patient and/or provide therapy to the heart of a patient.

In general, this disclosure is directed to techniques for estimating a cardiac chamber pressure or a vascular pressure based upon a measured impedance. A volume or dimension of the chamber or vessel may also be estimated. The estimated pressures and volumes may be absolute pressures or volumes, or changes in pressure or volume over time.

An elastance function (e.g., $E=\Delta P/\Delta V$) may be used to assist in determining the first relationship between volume and pressure. Elastance refers to the relationship between stress (i.e., manifest as pressure) and strain (i.e., the relative change in dimension or volume) of a cardiac chamber or a vascular lumen. Elastance is the inverse of compliance (C). The relationship between stress and strain, or alternatively between pressure and volume, in myocardial tissue is generally non-linear (i.e., non-Hookean). Thus, as the volume of the chambers increases, the elastance also increases. However, over a reasonably small range of volume, the elastance may be relatively constant. Thus, in some examples, a linear approximation of an elastance relationship over a small volume range may be used to estimate stress, or pressure, based upon estimates of strain, or volume.

A resistance function (e.g., $\rho=R*A/l$) may be used to assist in determining the second relationship between the measured impedance and volume, where $\rho$ is the resistivity material property of the tissue, R is the measured resistance between at least two electrodes located a unit distance apart assuming a uniform cross sectional area of the tissue sample, A. For example, the area or volume of a cardiovascular region of interest may be determined based upon the measured impedance, an estimate of the resistivity of the blood inside the region of interest, and an estimate of the distance between the measuring electrodes.

In general, the first relationship may include a directly proportional relationship between volume and pressure, and the second relationship may include an inversely proportional relationship between measured impedance and volume. In some examples, the first and second relationships may be combined to create an empirical inversely proportional relationship between measured impedance and cardiovascular pressure.

In some examples, a complex impedance may be measured that includes a resistive component (i.e., real component) and a reactive component (i.e., imaginary component). In general, blood is primarily a resistive material while tissues, such as the lipid bi-layer membrane constituting the cellular walls of the myocytes, are primarily capacitive. Therefore, myocardium has a greater reactive component of impedance than blood. An estimate of pressure or volume may be improved by extracting or isolating the real component from the measured complex impedance. In such a case, the real component may be indicative of the amount of blood within the chamber or vessel, which in turn may indicate the volume of the chamber. In some examples, the reactive component of the complex resistance may be used to determine an increase in tissue and thereby to assist in detecting hypertrophy of a chamber or lumen. Moreover, the reactive component may also be used to monitor and/or detect changes in tissue integrity, such as, e.g., changes in tissue integrity that occur during ischemia.

The estimation techniques described herein may be used to estimate real-time cardiovascular pressures or volumes. In some examples, mean pressures or mean volumes may be determined by, for example, determining the mean of a plurality of estimated pressures or volumes, such as by determining the mean over a time period, or by using a sliding window to determine the mean of the last N estimated volumes or pressures, and thereby smooth a pressure or volume trend.

Examples of cardiovascular pressures that may be estimated by using the techniques of this disclosure include left ventricular pressure, right ventricular pressure, left atrial pressure, right atrial pressure, arterial pressure, venous pressure, aortic pressure, and vena caval pressure. In addition, cardiovascular volume, strain, or dimension may be estimated alternatively, or in conjunction with, the pressure estimating techniques described herein. For example, techniques described in this disclosure may used to estimate left ventricular strain, right ventricular strain, left atrial strain, right atrial strain, arterial strain, and venous strain.

The impedance measurements may be taken by using leads and electrodes associated with conventional IMDs. In some examples, electrode combinations may be selected such that the resulting electric field is substantially confined to a cardiovascular region of interest. In additional examples, multiple pairs of electrodes may be selected to generate multiple electrical fields such that the composite electrical field is substantially homogenous over a cardiovascular region of interest. In further examples, a first set of electrodes may be selected for generating an electric field and a second set of electrodes may be selected for measuring the impedance of the resulting current. In any case, various combinations of electrodes may be selected and configured to tailor the pressure or volume estimation for a particular region of interest within a cardiovascular system.

FIG. 1 is a conceptual diagram illustrating an example therapy system 10 that may be used to monitor one or more physiological parameters of patient 14 and/or to provide therapy to heart 12 of patient 14. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 12 is ordinarily, but not necessarily, a human patient.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some alternative examples, therapy system 10 may include an additional lead or lead segment (not shown in FIG. 1) that deploys one or more electrodes within the vena cava or other vein, or within or near the aorta. These electrodes may allow alternative electrode configurations that may provide improved pressure or volume estimation for some chambers or vessels, for some applications, or for some patients.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device, computer workstation, or networked computing device. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure or volume, which may be estimated according to the techniques described herein. As another example, the user may use programmer 24 to retrieve information from IMD 16 regarding the performance or integrity of IMD 16 or other components of system 10, such as leads 18, 20 and 22, or a power source of IMD 16. As another example, the user may interact with programmer 24 to program, e.g., select parameters for, therapies provided by IMD 16, such as pacing, cardioversion and/or defibrillation.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

IMD 16 is an example of a device that may estimate a cardiac chamber pressure or volume, or a vascular pressure or volume, according to the techniques in this disclosure. In particular, IMD 16 may measure an impedance between two or more of electrodes, which may be attached to one or more of leads 18, 20, and 22, and estimate cardiac chamber pressure or volume based on the measured impedance.

Figure 2:
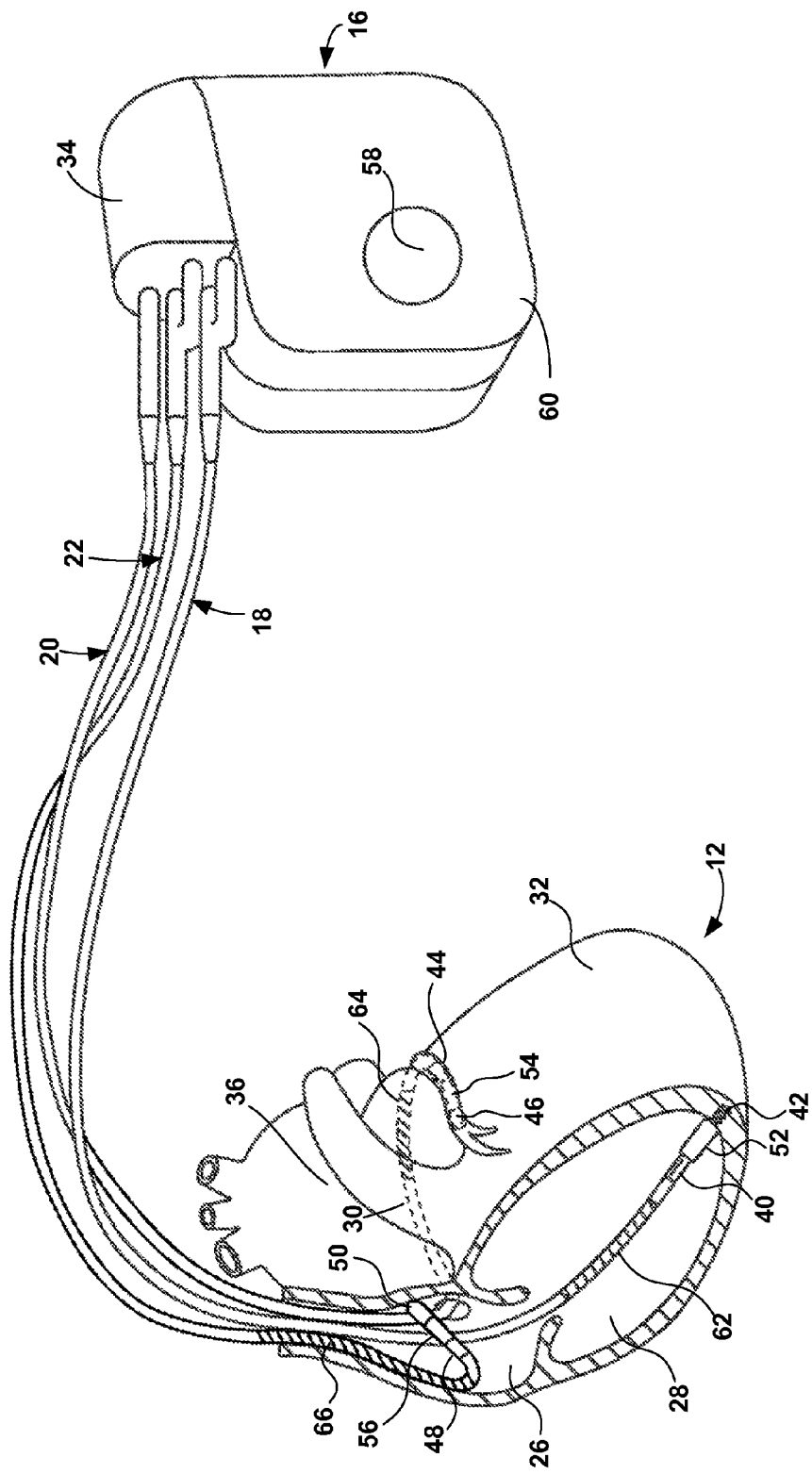
FIG. 2 is a conceptual diagram further illustrating the IMD and leads of the system of FIG. 1 in conjunction with the heart.

FIG. 2 is a conceptual diagram illustrating IMD 16 and leads 18, 20, 22 of therapy system 10 in greater detail. Leads 18, 20, 22 may be electrically coupled to a stimulation generator and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. There are no electrodes located in left atrium 36, but other examples may include electrodes in left atrium 36. Furthermore, other examples may include electrodes in other locations, such as the aorta or a vena cava, or epicardial or extra-cardial electrodes proximate to any of the chambers or vessels described herein Electrodes 40, 44, and 48 may take the form of ring electrodes, and electrodes 42, 46, and 50 may take the form of extendable helix tip electrodes mounted retractably within insulative electrode heads 52, 54, and 56, respectively. In other embodiments, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 58, 62, 64, and 66. The electrical signals are conducted to IMD 16 from the electrodes via the respective leads 18, 20, 22 or, in the case of housing electrode 58, a conductor couple to housing electrode 58. IMD 16 may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

Any combination of electrodes 40, 42, 44, 46, 48, 50, 60, 62, 64 and 66 may be used for measuring impedance in accordance with the techniques of this disclosure. In some examples a single pair of electrodes may be selected to generate an electrical field and to measure the impedance of the resulting current. For example, electrodes 42 and 46 may be used to generate an electrical field and to measure an impedance across left ventricle 32. In other examples, a first pair of electrodes may be selected to generate an electrical field and a second pair of electrodes may be selected to measure the impedance to the resulting current. For example, electrodes 42 and 46 may be used to generate a first electrical field, and electrodes 40 and 44 may be used to measure the impedance to the resulting current.

In further examples, multiple pairs of electrodes may be selected to generate multiple electrical fields. The electrodes may be selected such that the multiple electrical fields are substantially homogenous or uniform over the cardiovascular region of interest. For example, electrodes 42 and 46 may be used to generate a first electrical field, electrodes 62 and 64 may be used to generate a second electrical field, and electrodes 40 and 44 may be used to measure the impedance of the resulting current. The combined electrical field may be substantially homogeneous over portions of interest in left ventricle 32, thereby resulting in a more accurate estimation than if only a single pair of electrodes were used to generate a single electric field. In some examples, elongated electrodes 62, 64 and 66 may be used to generate uniform electric fields across a large region of interest.

In additional examples, multiple pairs of measurement electrodes may be selected to filter out extraneous impedance or "noise" resulting from the electrical fields traveling through regions that are not of interest. For example, electrodes 42 and 46 may generate a first electrical field across portions of right ventricle 28 and left ventricle 32 and a first impedance may be measured by electrodes 40 and 44. In addition, electrodes 42 and 62 may generate a second electrical field across portions of right ventricle 28 and a second impedance may be measured by electrodes 42 and 62. The first and second impedances may be subtracted or otherwise processed to determine the impedance associated with left ventricle 32, and a volume or pressure of the left ventricle may be estimated based on the first measured impedance. In this manner, multiple measurement electrodes may be used to subtract out "noise" within a measured signal, e.g., portions of the signal reflecting the impedance of one or more chambers or tissues not of interest, and thereby provide a more robust estimate of the pressure or volume for a cardiovascular region of interest.

The configuration of therapy system 10 illustrated in FIGS. 1 and 2 is merely one example. It should be understood that various other electrode and lead configurations for measuring impedance are within the scope of this disclosure. For example, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

Figure 3:
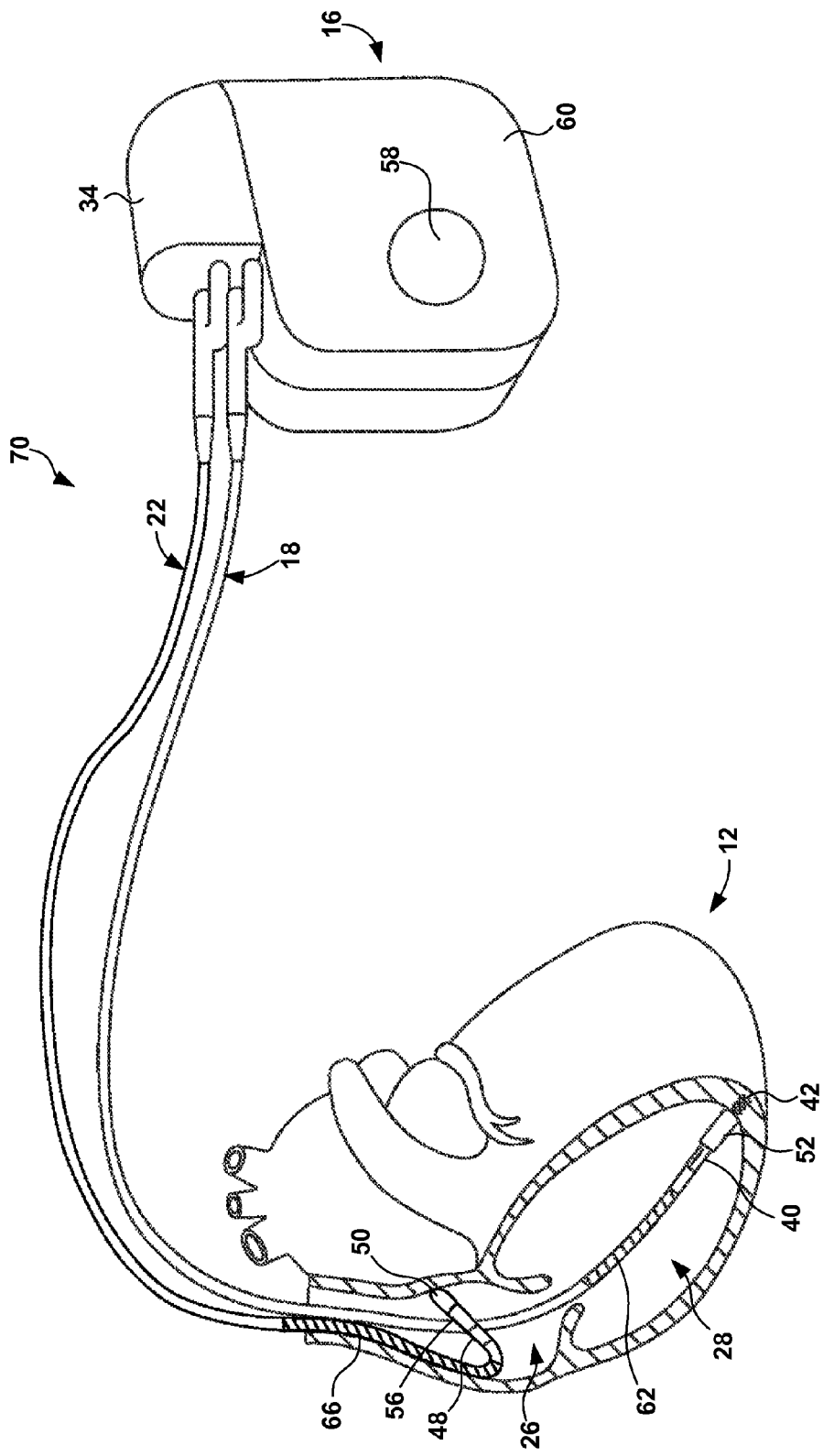
FIG. 3 is a conceptual diagram illustrating another example therapy system.

In addition, in other examples, a therapy system may include any suitable number of leads coupled to IMD 16, and each of the leads may extend to any location within or proximate to heart 12. Other examples of therapy systems may include three transvenous leads located as illustrated in FIGS. 1 and 2, and an additional lead located within or proximate to left atrium 36. Additional examples of therapy systems may include a single lead that extends from IMD 16 into right atrium 26 or right ventricle 28, or two leads that extend into a respective one of the right ventricle 26 and right atrium 26. An example of this type of therapy system is shown in FIG. 3. Any electrodes located on these additional leads may be used to measure an impedance in order to estimate a cardiovascular pressure according to techniques described herein.

FIG. 3 is a conceptual diagram illustrating another example of therapy system 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12. Estimating cardiovascular pressure or volume according to the techniques described herein may also be performed by or with respect to system 70.

Figure 4:
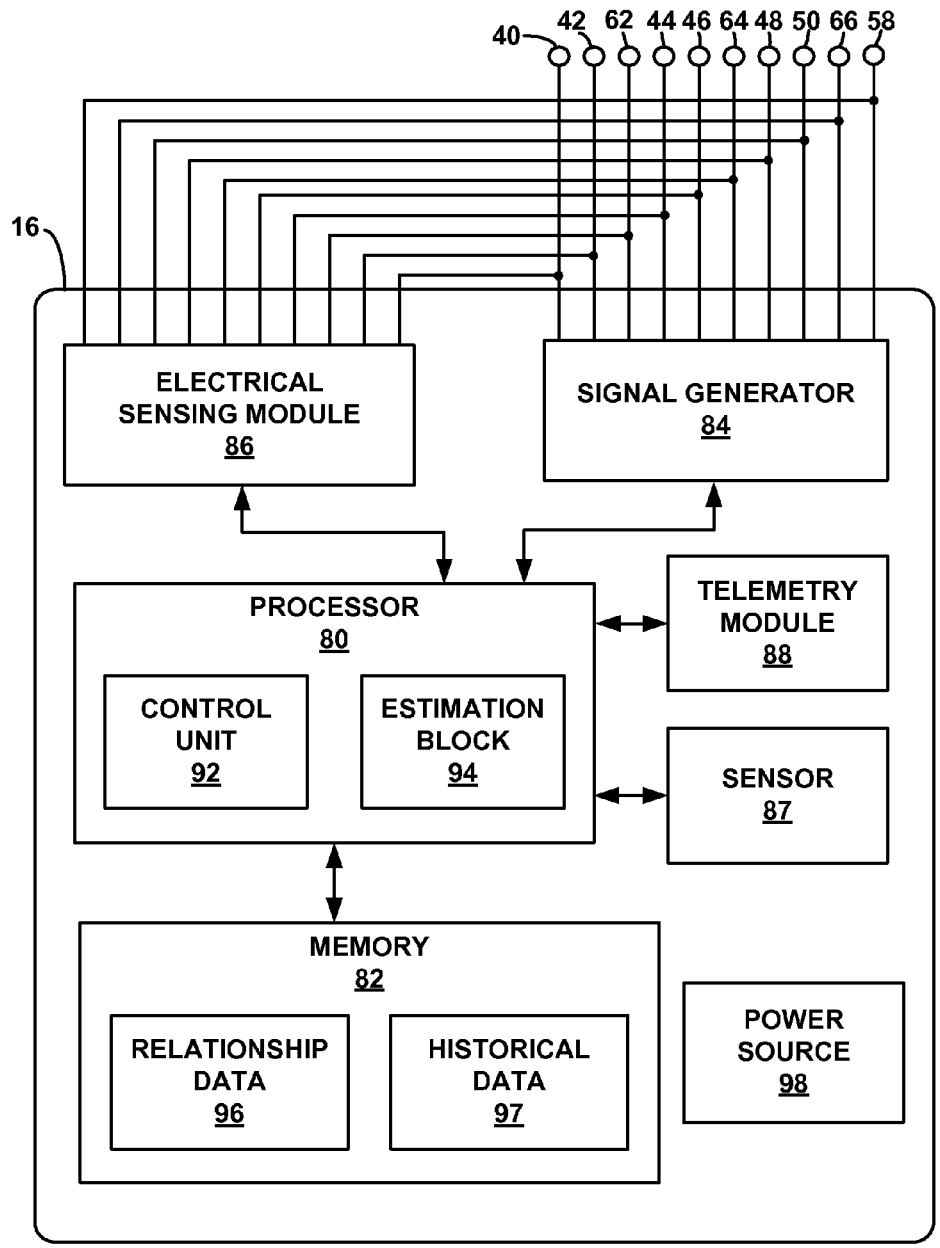
FIG. 4 is a functional block diagram illustrating an example configuration of an IMD.

FIG. 4 is a functional block diagram illustrating one example configuration of IMD 16. In the example illustrated by FIG. 4, IMD 16 includes a processor 80, memory 82, signal generator 84, electrical sensing module 86, telemetry module 88, and power source 98. Memory 82 may includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls stimulation generator 84 to deliver stimulation therapy to heart 12 according to a selected one or more of therapy programs, which may be stored in memory 82. In addition processor 80 is capable of estimating a cardiovascular pressure and/or volume according to the techniques described in this disclosure. To facilitate the estimation of cardiovascular pressure and volume, processor 80 is also capable of controlling electrode configurations and controlling the measurement of impedances across various combinations of electrodes.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator 84 may deliver one or more of these types of stimulation in the form of other signals, such as sine waves, square waves, or other substantially continuous time signals. According to the techniques in this disclosure, signal generator 84 may deliver signals to generate one or more electrical fields between at least two electrodes for impedance measurements.

Stimulation generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple a signal to selected electrodes.

Electrical sensing module 86 monitors signals from at least one of electrodes 40, 42, 44, 46, 48, 50, 58, 62, 64 or 66 in order to monitor electrical activity of heart 12. Electrical sensing module 86 may also include a switch module to select which of the available electrodes are used to sense the heart activity. In some examples, processor 80 may select the electrodes that function as sense electrodes, or the sensing configuration, via the switch module within electrical sensing module 86, e.g., by providing signals via a data/address bus. Electrical sensing module 86 includes multiple detection channels, each of which may comprise an amplifier. In some examples, electrical sensing module 86 or processor 80 may include an analog-to-digital converter for digitizing the signal received from a sensing channel for processing by processor 80. In response to the signals from processor 80, the switch module within electrical sensing module 86 may couple the outputs from the selected electrodes to one of the detection channels. In one example, electrical sensing module 86 may measure an impedance by application of an electrical field within the cardiovascular system. Processor 80 may control which of electrodes 40, 42, 44, 46, 48, 50, 58, 62, 64 and 66 is coupled to sensing module 86 for impedance measurements, e.g., via the switching module.

Processor 80 may estimate a cardiovascular pressure and/or a cardiovascular volume based upon a measured impedance and one or more relationships stored in memory 82. Processor 80 includes a control unit 92 and an estimation block 94. Control unit 92 controls the selection of electrode configurations and the measurement of impedances for estimating a pressure or volume for a cardiovascular chamber of interest. Control unit 92 may communicate with signal generator 84 to select two or more stimulation electrodes in order to generate one or more electrical fields across a cardiovascular region of interest. Control unit 92 may also communicate with electrical sensing module 86 to select two or more measurement electrodes based upon the region of interest to be measured. As discussed above, the signal and sensing electrodes may be the same electrodes.

Control unit 92 may select multiple pairs of electrodes for signal delivery and measurement depending upon the estimation algorithm. For example, control unit 92 may select two or more signal delivery electrodes proximate to a cardiovascular region of interest such that the resulting electrical field is substantially confined to the region of interest. As another example, control unit 92 may select multiple pairs of signal delivery electrodes for generating multiple electrical fields such that the composite electrical field is substantially homogenous over the region of interest. In a further example, control unit 92 may select multiple pairs of measurement electrodes to cancel out measurement "noise" associated with other regions that are not part of the region of interest.

In some examples, control unit 92 may also select one or more relationships stored in memory 82 to assist in the estimation of a cardiovascular pressure or volume by estimation block 94. Control unit 92 may select a relationship from a set of one or more relationships between volume and pressure and/or between strain and stress. In addition, control unit 92 may also select a relationship from a set of one or more relationships between impedance and volume and/or between impedance and strain. In examples where a composite relationship is generated, control unit 92 may select a relationship from a set of one or more relationships between impedance and pressure.

Control unit 92 may select the relationships based on various criteria. For example, control unit 92 may select a relationship based upon the cardiac chamber or vascular lumen to be measured. As another example, control unit 92 may select a relationship based upon a type of patient or based upon a particular condition that a patient is suffering from. In some examples, a predetermined relationship may be configured or tailored to a specific patient, a specific condition, or a specific measurement objective. In any case, control unit 92 may retrieve the selected relationships from memory 82 and deliver the relationships to estimation block 94 for use in estimating a pressure or volume of a cardiovascular chamber or lumen.

Estimation block 94 may estimate a pressure or a volume of an element of a cardiovascular system based upon a measured impedance. Estimation block 94 may utilize a relationship between volume and pressure or, alternatively, between strain and stress to assist in the estimation. In some examples the relationship may be represented by an elastance or compliance function derived from empirical data. In additional examples, the relationship may be a linear approximation of an elastance function over a relatively small volume interval.

As an example, the elastance or compliance function may be determined based on one or more data sets from a population of patients. In such an example, the resulting elastance function may be determined by matching one or more characteristics of the patient for which the elastance function is being calibrated with one or more patients within the population who have similar characteristics. When a patient is found within the population that is a close match, the data set associated with the matching patient may be used to determine an elastance function for the patient for whom the elastance function is being calibrated. In another example, the elastance or compliance function may be determined on an individual patient basis by forming a calibration factor specific to the individual patient. The calibration factor may be determined by acute invasive pressure measurements in one example. Once this calibration factor is determined, the calibration factor may remain constant until another calibration is performed. In further examples, a combination approach may be used that first determines one or more patients within the population of patients that have matching characteristics, chooses one or more elastance functions associated with the matching patients, derives a composite elastance function based on the chosen elastance functions, and tailors the composite elastance function to the particular patient who is being fitted with the implantable medical device. Example characteristics or matching criteria that may be used for determining an appropriate elastance function include patient physiology, patient measurement parameters, patient health history, and/ or a particular cardiovascular event that the patient is experiencing or is at risk for experiencing. The cardiovascular event may include systolic dysfunction, diastolic dysfunction, congestive heart failure, hypertrophying, myocardial tissue degradation, and/or any other cardiovascular event that may occur within a patient. The patient measurement parameters may include cardiovascular pressure, cardiovascular volume, or any other parameters that provide measurements of various aspects of the cardiovascular system of the patient.

In some examples, estimation block 94 may estimate a change in pressure based on a relationship between a change in volume and a change in pressure. In addition, estimation block 94 may use an additional relationship between a measured change in impedance and a change in volume to assist in estimating the change in pressure and/or the change in volume.

Memory 82 may include relationship data 96 and historical data 97. Relationship data 96 may include predetermined relationships, derived relationships, and empirical relationships between two or more parameters. For example, relationship data 96 may include relationships between impedance and volume; impedance and strain; volume and pressure; strain and stress; impedance and stress; and impedance and pressure. Relationship data 96 may use historical data 97 for a particular patient or condition to derive new relationships or to configure existing relationships for use by estimation block 94.

Relationship data 96 may include an elastance function (e.g., $E=\Delta P/\Delta V$) where E is the elastance, $\Delta P$ is a change in pressure or stress and $\Delta V$ is a change in volume or strain. Because the elastance function for myocardial tissue is generally non-linear (i.e., non-Hookean), some examples may use a linear approximation of an elastance relationship over a small volume interval in order to efficiently estimate pressure without having to store complex functions in a look-up table.

Relationship data 96 may also include a resistance function (e.g., $\rho=R*A/l$) where $\rho$ is the resistivity of the blood between the electrodes, R is a resistance or impedance measured by the electrodes, A is the cross-sectional area of the region of interest, and l is a distance between the electrodes. The resistance function may be modified in order to derive a relationship between volume and measured impedance. Such a function may take on the following form: $V=\rho*l^2/R$ where V is the volume of the chamber or lumen between the electrodes. In general, the volume function illustrates that an inversely proportional relationship may be established between measured impedance and volume.

Historical data 97 may include, for example, impedance measurements, estimated pressures, estimated volumes, other processed or estimated values for a given patient or medical device, or trends of such data over time. In some examples, memory 82 may include a buffer for storing estimated pressures, estimated volumes, or other estimated or measured values, to facilitate processor 80 in determining mean, median, or other processed values based thereon. Such processed values may be stored in memory 82 as historical data 97.

Control unit 92 may retrieve and use historical data 97 to determine what type of relationship should be used by estimation block 94. In some examples, control unit 92 may use historical data 97 to further configure the relationships. In additional examples, historical data 97 may include intervals, such as P-P, A-V, R-R, or R-T intervals, which processor 80 may use to synchronize the impedance measurements such that the impedance measurements are taken at a particular time during the cardiac cycle, e.g., to determine a particular pressure or volume of a cardiovascular region of interest.

In addition, processor 80 may store cardiac electrograms (EGMs) for physiological episodes, such as tachyarrhythmias, within historical data 97 of memory 82. For example, processor 80 may store cardiac EGMs for atrial and ventricular tachycardia and fibrillation episodes, in response to the detection of the tachycardia or fibrillation using any of the techniques described above.

During pacing, escape interval counters maintained by processor 80 may be reset upon sensing of R-waves and P-waves with detection channels of electrical sensing module 86. Stimulation generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions.

The value of the count present in the escape interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to synchronize the impedance measurements over several cardiac cycles or to ensure that impedance measurements occur at particular time within the cardiac cycle. In addition, processor 80 may use the count in the interval counters to detect a tachyarrhythmia event, such as an atrial or ventricular fibrillation or tachycardia.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrogram signals) produced by atrial and ventricular sense amp circuits within electrical sensing module 86 to programmer 24. Programmer 24 may interrogate IMD 16 to receive the electrograms. Processor 80 may store electrograms within memory 82, and retrieve stored electrograms from memory 82. Processor 80 may also generate and store marker codes indicative of different cardiac events that electrical sensing module 86 detects, such as ventricular and atrial depolarizations, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. Additionally, processor 80 may store historical data 97 regarding estimated volumes and/or pressures in memory 82, and may provide such data to programmer 24 or another external device via telemetry circuit 88. In some examples, processor 80 may provide such data with a time-correlated electrogram and/or marker channel.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis.

Figure 5:
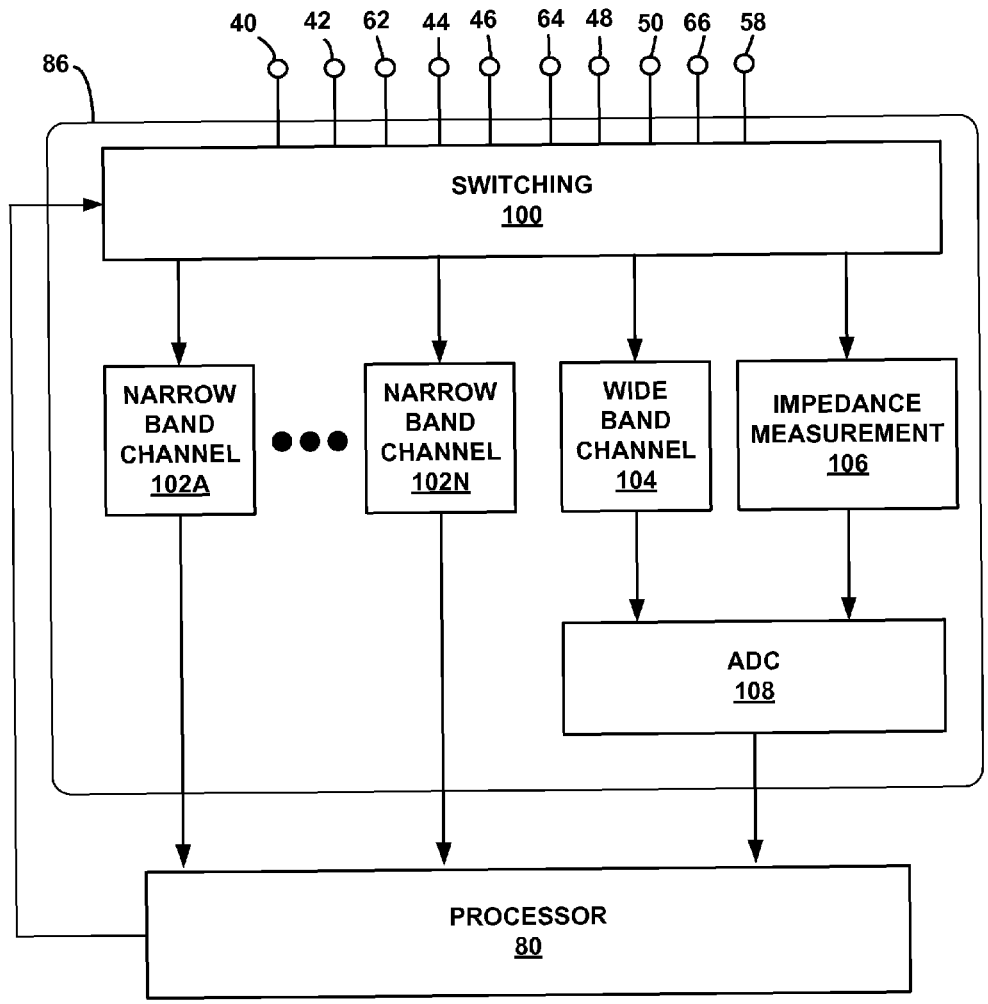
FIG. 5 is a functional block diagram illustrating an example electrical sensing module of an IMD.

FIG. 5 is a block diagram of an example configuration of electrical sensing module 86. As shown in FIG. 5, electrical sensing module 86 includes multiple components including switching module 100, narrow band channels 102A to 102N, wide band channel 104, impedance measurement module 106, and analog to digital converter (ADC) 108. Switching module 100 may, based on control signals from processor 80, control which of electrodes 40, 42, 44, 46, 48, 50, 58, 62, 64 and 66 is coupled to which of channels 102 and 104 and impedance measurement module 106, at any given time.

Each of narrow band channels 102 may comprise a narrow band filtered sense-amplifier that compares the detected signal to a threshold. If the filtered and amplified signal is greater than the threshold, the narrow band channel indicates that a certain electrical heart event has occurred. Processor 80 then uses that detection in measuring frequencies of the detected events. Narrow band channels 102 may have distinct functions. For example, some various narrow band channels may be used to detect either atrial or ventricular events.

In one example, at least one narrow band channel 102 may include an R-wave amplifier that receives signals from the sensing configuration of electrodes 40 and 42, which are used for sensing and/or pacing in right ventricle 28 of heart 12. Another narrow band channel 102 may include another R-wave amplifier that receives signals from the sensing configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel 102 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

Wide band channel 104 may comprise an amplifier with a relatively wider pass band than the R-wave or P-wave amplifiers. Signals from the selected sensing electrodes that are selected for coupling to this wide-band amplifier may be converted to multi-bit digital signals by ADC 108. In some examples, processor 80 may store signals the digitized versions of signals from wide band channel 104 in memory 82 as EGMs. In some examples, the storage of such EGMs in memory 82 may be under the control of a direct memory access circuit.

In some examples, processor 80 may employ digital signal analysis techniques to characterize the digitized signals from wide band channel 104 to, for example detect and classify the patient's heart rhythm. Processor 80 may detect and classify the patient's heart rhythm by employing any of the numerous signal processing methodologies known in the art. Further, in some examples, processor 80 may analyze the morphology of the digitized signals from wide band channel 104 to distinguish between noise and cardiac depolarizations.

Additionally, in some examples, processor 80, e.g., control unit 92, may analyze the timing and/or morphology of the digitized signals, or the timing of indications from narrow-band channels 102, to control the timing of impedance measurements for pressure and/or volume estimation as described herein. In some examples, the pressure or volume of a particular chamber or vessel at a certain point during the mechanical cardiac cycle may be of interest. For example, control unit 92 may control the timing of impedance measurements during systole to detect a systolic pressure, such as a left ventricular systolic pressure that may be relevant to diagnosing or monitoring heart failure. As another example, control unit 92 may control the timing measurements during diastole to detect a diastolic volume, such as a left ventricular end diastolic volume (LVEDV), which may also be relevant to diagnosing or monitoring heart failure. As another example, control unit 92 may control the timing measurements during diastole to detect a diastolic pressure, such as a right ventricular diastolic pressure, which may be used to estimate pulmonary artery pressure, which may be relevant to monitoring heart failure.

Sensing module 86 and/or processor 80 are capable of collecting, measuring, and/or calculating impedance data utilizing any two or more of electrodes 40, 42, 44, 46, 48, 50, 58, 62, 64 and 66. In some examples, impedance measurement module 106 may measure electrical parameter values during delivery of an electrical signal between at least two of the electrodes. Processor 80 may control signal generator 84 to deliver the electrical signal between the electrodes. Processor 80 may determine impedance values based on parameter values measured by impedance measurement module 106, and store measured impedance values in memory 82.

In some examples, processor 80 may perform an impedance measurement by controlling delivery, from signal generator 84, of a voltage pulse between first and second electrodes. The voltage pulse may generate an electrical field between the first and second electrodes. Measurement module 106 may measure a resulting current, and processor 80 may calculate an impedance based upon the voltage amplitude of the pulse and the measured amplitude of the resulting current. In other examples, processor 80 may perform an impedance measurement by controlling delivery, from signal generator 84, of a current pulse between first and second electrodes. The current pulse may generate an electrical field between the first and second electrodes. Measurement module 106 may measure a resulting voltage, and processor 80 may calculate an impedance based upon the current amplitude of the pulse and the measured amplitude of the resulting voltage. Measurement module 106 may include circuitry for measuring amplitudes of resulting currents or voltages, such as sample and hold circuitry.

In these examples, signal generator 84 delivers signals that do not necessarily deliver stimulation therapy to heart 12, due to, for example, the amplitudes of such signals and/or the timing of delivery of such signals. For example, these signals may comprise sub-threshold amplitude signals that may not stimulate heart 12. In some cases, these signals may be delivered during a refractory period, in which case they also may not stimulate heart 12. IMD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue.

In certain cases, IMD 16 may measure impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components. Impedance data may include actual, measured impedance values, or may include values that can be used to calculate impedance (such as current and/or voltage values).

In some examples in which impedance measurement module 106 measures impedance values including both a resistive and reactive component, processor 80 may process digitized versions of these signals to separate the real and reactive components. In other examples, impedance measurement module 106 may include circuitry to selective provide one or both of the real or reactive components. For example, impedance measurement module 106 may include one or more chopper stabilized instrumentation amplifiers for selectively providing one or both the real or reactive components. An example, chopper stabilized instrumentation amplifier for this purpose is described in commonly-assigned U.S. Pat. No. 7,391,257 to Denison et al., entitled "CHOPPER-STABILIZED INSTRUMENTATION AMPLIFIER FOR IMPEDANCE MEASURMENT," which issued on Jun. 24, 2008, and is incorporated herein by reference in its entirety.

According to the techniques in this disclosure, IMD 16 may estimate a pressure or volume of a cardiac chamber or vascular lumen based on the measured impedance. In some examples, impedance measurement block 106 may isolate a real component of the impedance to assist in this calculation. Impedance measurement block 106 may gather impedance measurements from multiple combinations of electrodes either simultaneously or at specified time intervals depending on the instructions received by electrical sensing module 86 from control unit 92.

Figure 6:
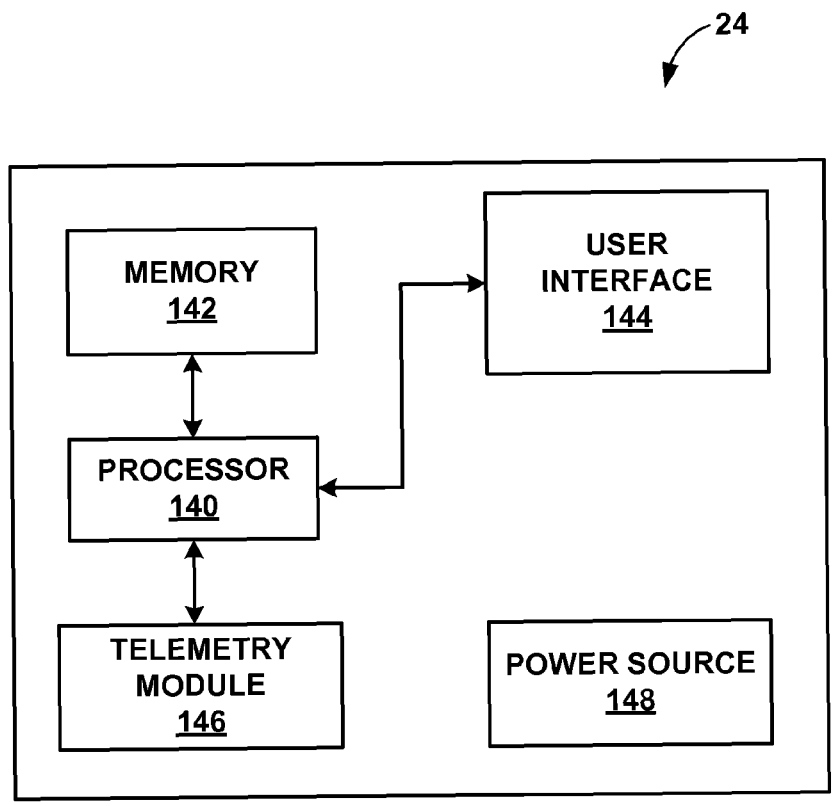
FIG. 6 is a functional block diagram of an example external programmer that facilitates user communication with the IMD.

FIG. 6 is block diagram of an example programmer 24. As shown in FIG. 6, programmer 24 includes processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 144 which may include display to present graphical user interface to a user, and a keypad or another mechanism for receiving input from a user.

Processor 14 can take the form one or more microprocessors, DSPs, ASICs, FPGAs, programmable logic circuitry, or the like, and the functions attributed to processor 102 herein may be embodied as hardware, firmware, software or any combination thereof. Memory 142 may store instructions that cause processor 140 to provide the functionality ascribed to programmer 24 herein, and information used by processor 140 to provide the functionality ascribed to programmer 24 herein. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 102, which may be coupled to an internal antenna or an external antenna. An external antenna that is coupled to programmer 24 may correspond to the programming head that may be placed over heart 12, as described above with reference to FIG. 1. Telemetry module 142 may be similar to telemetry module 88 of IMD 16 (FIG. 4).

Telemetry module 142 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

Processor 140 of programmer 24 may implement any of the techniques described herein, or otherwise perform any of the methods described below. For example, processor 140 of programmer 24 may estimate pressures or volumes using any of the techniques herein based on impedance measurements received from IMD 16. Processor 140 of programmer 24 may, in some examples, control the timing and configuration of impedance measurements by IMD 16.

Figure 7:
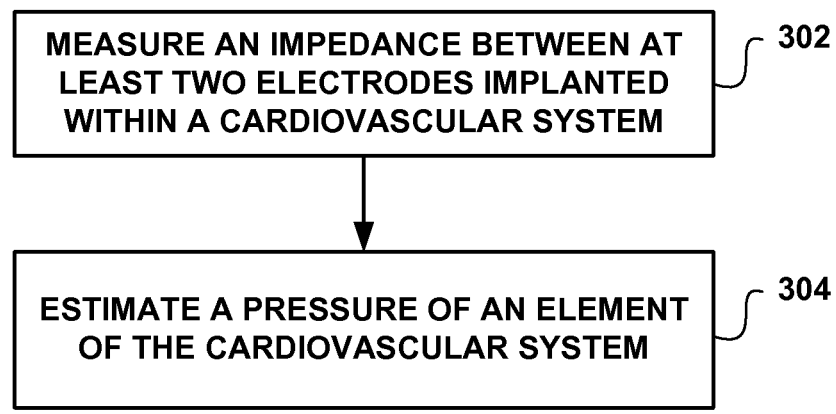
FIG. 7 is a flow diagram illustrating an example method for estimating a pressure of an element of a cardiovascular system.

FIG. 7 is a flow diagram illustrating an example method for estimating a pressure of an element of a cardiovascular system, which may be performed by any processor or module described herein, or combination thereof. According to FIG. 7, impedance measuring block 106 may measure an impedance between at least two electrodes implanted within a cardiovascular system (302). Processor 80 may estimate a pressure of an element of the cardiovascular system based on a relationship between the measured impedance and volume of the element of the cardiovascular system and based on a relationship between volume and pressure (304). The element of the cardiovascular system may include a cardiac chamber or a vascular lumen. In some examples, impedance measurement module 106 may measure a change in impedance, and processor 80 may estimate a change in pressure based on a relationship between the measured change in impedance and a change in volume of the element of the cardiovascular system and based on a relationship between the change in volume and the change in pressure.

Figure 8:
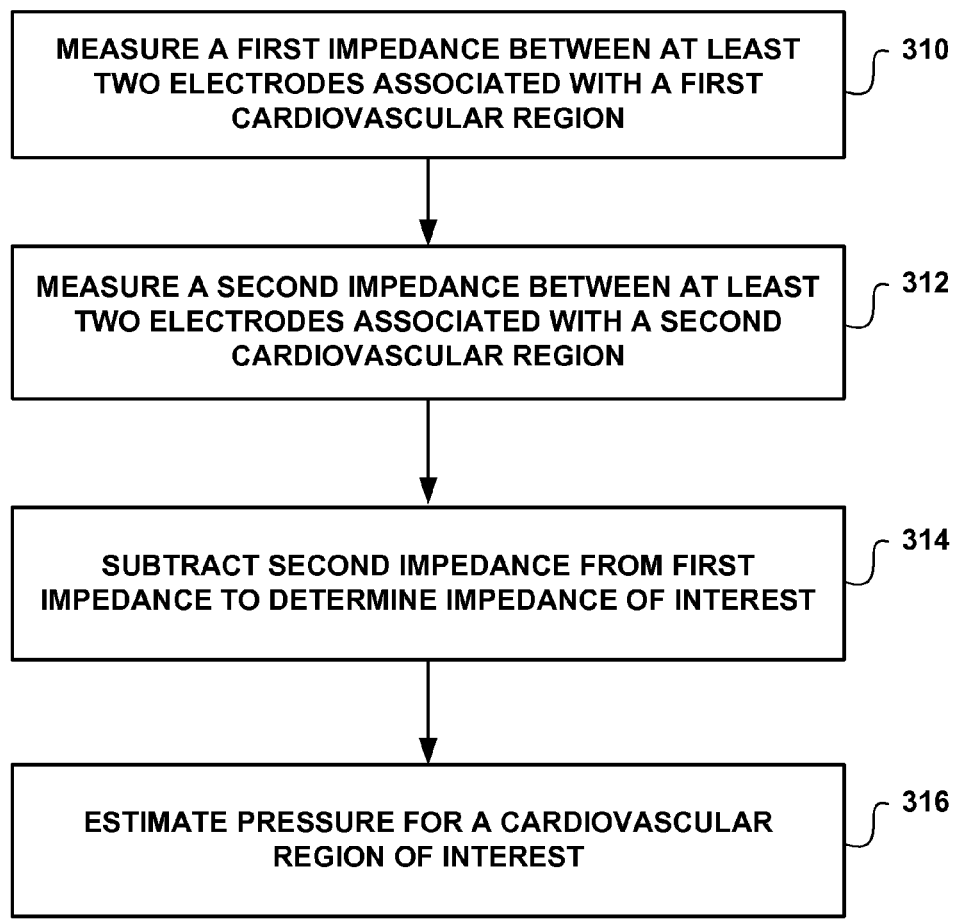
FIG. 8 is a flow diagram illustrating an example method for estimating a pressure of an element of a cardiovascular system by using multiple impedance measurements.

FIG. 8 is a flow diagram illustrating another example method for estimating a pressure of an element of a cardiovascular system, which may be performed by any processor or module described herein, or combination thereof. According to FIG. 8, impedance measurement module 106 may measure a first impedance between at least two electrodes associated with a first cardiovascular region (310). Impedance measurement module 106 may also measure a second impedance between at least two electrodes associated with a second cardiovascular region (312). The first and second impedances may be measured at the same or different times.

Processor 80 may subtract the second impedance, which represents impedance in a chamber or region that is not of interest, from the first impedance, which may include impedance in a chamber or region of interest as well as impedance in the chamber or region not of interest (314). Processor 80 may then estimate pressure (or volume) for the region of interest based on a relationship between the impedance of interest and volume and based on a relationship between the volume and the second pressure (316).

Figure 9:
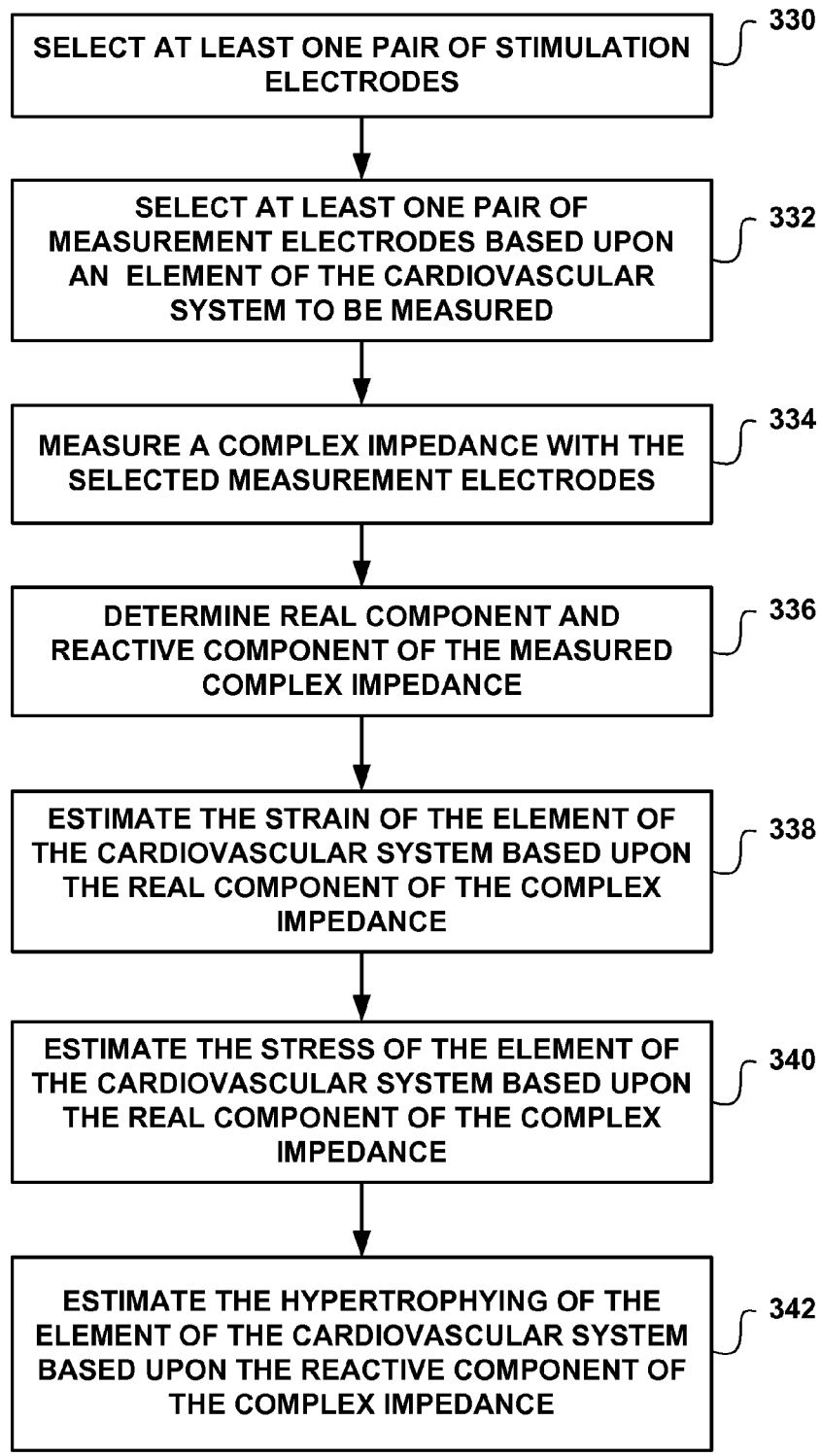
FIG. 9 is a flow diagram illustrating an example method for estimating strain, stress and/or hypertrophying of an element of a cardiovascular system by isolating the real and reactive components of a complex impedance.

FIG. 9 is a flow diagram illustrating an example method for estimating the stress, strain, and hypertrophying of an element of a cardiovascular system by isolating the real component of a complex impedance, which may be performed by any processor or module described herein, or combination thereof. According to FIG. 9, control unit 92 selects at least one pair of stimulation electrodes (330). Control unit 92 also selects at least one pair of measurement electrodes based upon an element of the cardiovascular system to be measured (332). Impedance measurement module 106 measures a complex impedance with the selected measurement electrodes (334). Impedance measurement module 106 or processor 80 calculates a real component and a reactive component of the measured complex impedance (336).

Estimation block 94 estimates the strain or volume of the element of interest in the cardiovascular system based upon the real component of the complex impedance (338). Estimation block 94 may use a relationship between measured impedance and strain or a relationship between measured impedance and volume to assist in the estimation.

Estimation block 94 estimates the stress or pressure of the element of interest in the cardiovascular system based upon the real component of the complex impedance (340). Estimation block 94 may use a relationship between strain and stress or a relationship between volume and pressure to assist in the estimation. Estimation block 94 may also use the estimated strain or volume from step 338 to assist in the estimation.

Processor 80 estimates a change in size of an element of the cardiovascular system. In some examples, processor 80 may estimate the hypertrophying of the element of the cardiovascular system based upon the reactive component of the complex impedance (342). In other examples, processor 80 may estimate myocardial degradation of the element of the cardiovascular system due to ischemia based upon the reactive component of the complex impedance. In any case, the estimate may be based upon empirical data that relates complex impedance to a change in size, such as hypertrophying or myocardial tissue degradation, of a particular cardiovascular region of interest. In other examples, the estimate may be based upon a baseline complex impedance. When the measured complex impedance deviates from the baseline complex impedance hypertrophying or myocardial tissue degradation may be detected or estimated.

In some examples, processor 80 may provide an indicator of hypertrophying of the element of the cardiovascular system based upon the reactive component of the complex impedance. In other examples, processor 80 may provide an indicator of myocardial tissue degradation of an element of the cardiovascular system due to ischemia in addition to, or in the alternative to, the indicator of hypertrophying. The indicator may include a signal, a sound, a notification sent to the programmer, a displayed message, or any other alert or notification to the patient or physician of the hypertrophying or tissue degradation condition.

Figure 10:
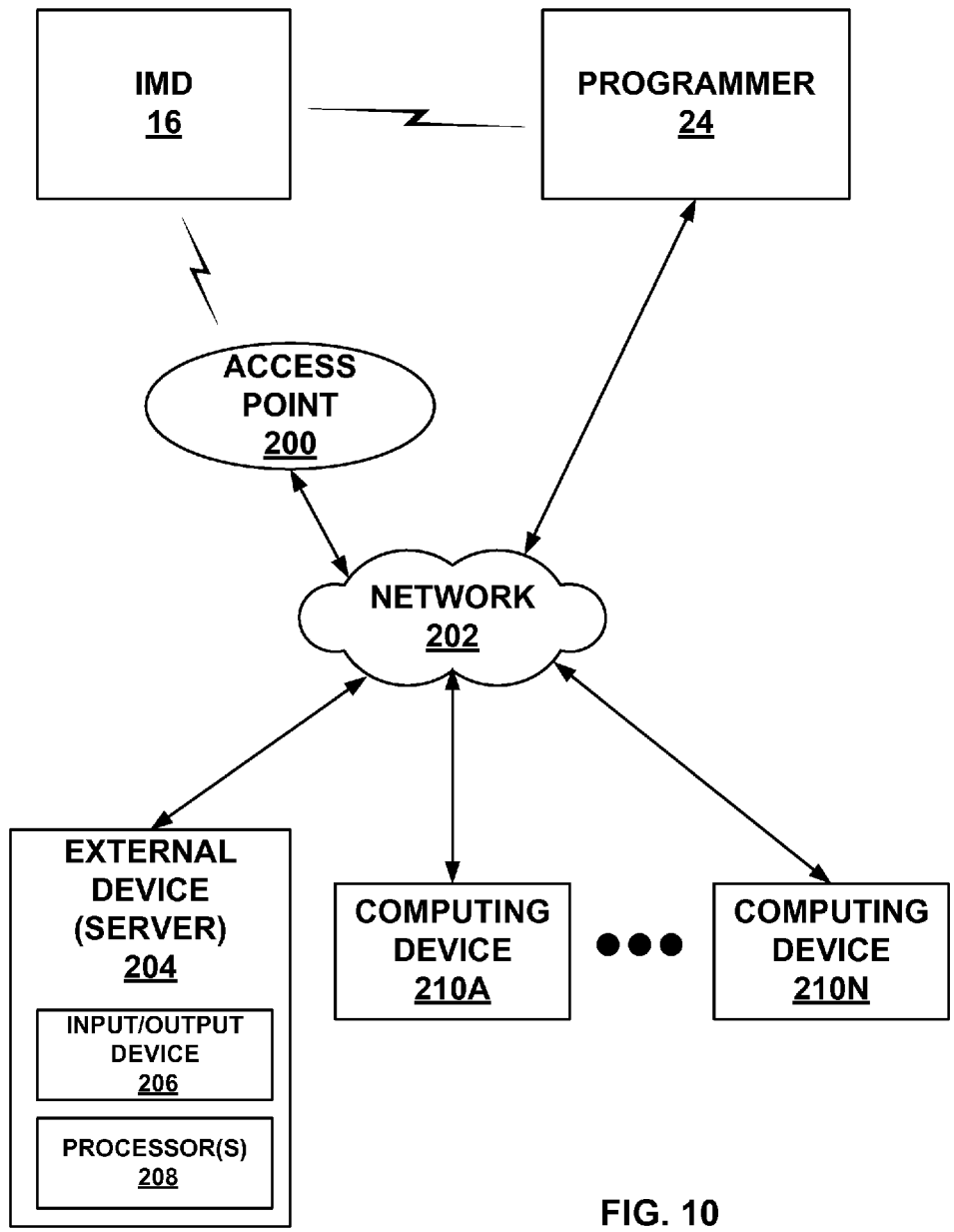
FIG. 10 is a block diagram illustrating an example system that includes an external device, such as a server, and one or more computing devices that are coupled to the IMD and programmer shown in FIG. 1 via a network.

FIG. 10 is a block diagram illustrating an example system that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 10, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 186 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16.

In some examples, access point, 200, server 204 or computing devices 210 may perform any of the various functions or operations described herein. For example, processor 208 of server 204 may estimate pressures or volumes using any of the techniques herein based on impedance measurements received from IMD 16 via network 202. Processor 208 of server 204 may, in some examples, control the timing and configuration of impedance measurements by IMD 16 via network 202 and access point 200.

In some cases, server 204 may be configured to provide a secure storage site for historical data 97 (FIG. 4) that has been collected from IMD 16 and/or programmer 24. Network 202 may comprise a local area network, wide area network, or global network, such as the Internet. In some cases, programmer 24 or server 206 may assemble historical data 97 in web pages or other documents for viewing by and trained professionals, such as clinicians, via viewing terminals associated with computing devices 210A-210N. The illustrated system of FIG. 10 may be implemented, in some aspects, with general network technology and functionality similar to that provided by the Medtronic CareLink® Network developed by Medtronic, Inc., of Minneapolis, Minn.

Although the disclosure is described with respect to lead and electrode configurations implanted proximate to a heart, such techniques may be applicable to leads and electrodes implanted proximate to other areas within cardiovascular system such as, e.g., pulmonary arteries, pulmonary veins, the aorta, the vena cava, and the like. In such devices, the techniques described in this disclosure may be applied to estimate volume and pressure of the cardiovascular element of interest.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following example statements.

The invention claimed is:

1. A method comprising:
storing in a memory of an implantable medical device a plurality of relationships between volume and pressure, the plurality of relatioships comprising a relationship between volume and pressure in avascular lumen;
storing in the memory a plurality of relationships between impedence and volume;
measuring an impedance between at least two electrodes implanted within or proximate to a cardiovascular system of a patient;
enabling a control unit to select one of the stored plurality of relationships between volume and pressure and one of the stored plurality of relationships between impedence and volume based on at least one selection criterion; and
estimating by the control unit, a pressure of an element of the cardiovascular system based on the selected relationship between impedence and volume and the selected relationship between the volume and the pressure, wherein the relationship between the volume and the pressure comprises an elastance function derived from empirical data comprising historical data of the patient.

2. The method of claim 1, wherein the element of the cardiovascular system comprises one of a cardiac chamber or a vascular lumen.

3. The method of claim 1, wherein relationship between the measured impedance and the volume comprises an inversely proportional relationship.

4. The method of claim 1,
wherein the relationship between the volume and the pressure comprises a linear approximation of the elastance function for a given volume interval.

5. The method of claim 1, further comprising:
selecting the relationship between the volume and the pressure from the plurality of relationships based upon a particular characteristic of the patient.

6. The method of claim 1,
wherein measuring the impedance comprises measuring a change in impedance,
wherein estimating the pressure comprises estimating a change in pressure based on a relationship between the measured change in impedance and a change in volume of the element of the cardiovascular system and based on a relationship between the change in volume and the change in pressure.

7. The method of claim 1, further comprising:
selecting a combination of electrodes as the at least two electrodes based upon the element of the cardiovascular system to be measured.

8. The method of claim 1, wherein measuring the impedance comprises:
generating a plurality of electric fields between the at least two electrodes;
applying the plurality of electric fields to the element of the cardiovascular system such that the combined electric field is substantially homogeneous over the element; and
measuring an impedance of a resultant current flow between the at least two electrodes.

9. The method of claim 1, wherein measuring the impedance comprises:
measuring a first impedance for a first region;
measuring a second impedance for a second region; and
subtracting the second impedance from the first impedance to determine an impedance for the element.

10. The method of claim 1, wherein the measured impedance comprises a real component and a reactive component, and estimating a pressure comprises estimating the pressure based on the real component.

11. The method of claim 1, further comprising estimating a volume of the element based on the relationship between impedance and volume.

12. The method of claim 1, wherein measuring the impedance comprises measuring a complex impedance between the at least two electrodes, wherein the method further comprises determining a real component of the complex impedance, and wherein estimating the pressure comprises estimating the pressure of the element of the cardiovascular system based on a relationship between the real component of the complex impedance and volume and the relationship between the volume and the pressure.

13. The method of claim 1, wherein measuring the impedance comprises measuring a complex impedance between the at least two electrodes, and wherein the method further comprises:
determining a reactive component of the complex impedance; and
providing at least one of an indicator of hypertrophying of the element of the cardiovascular system and an indicator of myocardial tissue degradation of the element of the cardiovascular system due to ischemia based upon the reactive component of the complex impedance.

14. An implantable medical device comprising:
an impedance measurement module configured to measure an impedance between at least two electrodes implanted within a cardiovascular system of a patient;
a memory configured to store data representing a relationship between impedance and volume, and a relationship between the volume and pressure, wherein the relationship between the volume and the pressure comprises an elastance function derived from empirical data comprising historical data of the patient, the memory storing a plurality of relationships between volume and pressure, the plurality of relationships comprising a relationship between volume and pressure in a vascular lumen, the memory storing a plurality of relationships between impedance and volume; and
a processor configured to select one of the stored plurality of relationships between volume and pressure from the memory and, based upon at least one selection criterion, select one of the stored plurality of relationships between impedance and volume, and estimate a pressure of an element of the cardiovascular system based on the stored data and the selected relationships.

15. The device of claim 14, wherein the relationship between the measured impedance and the volume comprises an inversely proportional relationship.

16. The device of claim 14,
wherein the relationship between the volume and the pressure comprises
a linear approximation of the elastance function for a given volume interval.

17. The device of claim 14, wherein the processor further comprises:
a control unit configured to select the relationship between the volume and the pressure from the plurality of relationships based upon a particular patient type.

18. The device of claim 14,
wherein the impedance measuring measurement is further configured to measure a change in impedance,
wherein the processor is further configured to estimate a change in pressure based on a relationship between the measured change in impedance and a change in volume of the element of the cardiovascular system and based on a relationship between the change in volume and the change in pressure.

19. The device of claim 14, wherein the processor further comprises a control unit configured to select a combination of electrodes as the at least two electrodes based upon the element of the cardiovascular system to be measured.

20. The device of claim 14, wherein the impedance measurement module is further configured to measure the impedance the at least in part by:
generating a plurality of electric fields between the at least two electrodes;
applying the plurality of electric fields to the element of the cardiovascular system such that the combined electric field is substantially homogeneous over the element; and
measuring an impedance of a resultant current flow between the at least two electrodes.

21. The device of claim 14, wherein the impedance measurement module is further configured to measure a complex impedance between the at least two electrodes, and wherein the processor is further configured to determine a real component of the complex impedance, and estimate the pressure of the element of the cardiovascular system based on a relationship between the real component of the complex impedance and volume and the relationship between the volume and the pressure.

22. The device of claim 14, wherein the impedance measurement module is further configured to measure a complex impedance between the at least two electrodes, and wherein the processor is further configured to determine a reactive component of the complex impedance, and provide at least one of an indicator of hypertrophying of the element of the cardiovascular system and an indicator of myocardial tissue degradation of the element of the cardiovascular system due to ischemia based upon the reactive component of the complex impedance.

23. A system comprising:
means for storing a plurality of relationships between volume and pressure, the plurality of relationships comprising a relationship between volume and pressure in a vascular lumen;
means for storing a plurality of relationships between impedance and volume;
means for measuring an impedance between at least two electrodes implanted within a cardiovascular system of a patient;
means for selecting one of the stored plurality of relationships between volume and pressure;
means for selecting one of the stored plurality of relationships between impedance and volume based upon at least one selection criterion; and
means for estimating a pressure of an element of the cardiovascular system based on the selected relationship between impedance and volume and based on the selected relationship between volume and pressure, wherein the relationship between the volume and the pressure comprises an elastance function derived from empirical data comprising historical data of the patient.

24. The system of claim 23, wherein the element of the cardiovascular system comprises one of a cardiac chamber or a vascular lumen.

25. The system of claim 23, wherein the relationship between the measured impedance and the volume comprises an inversely proportional relationship.

26. The system of claim 23,
wherein the relationship between the volume and the pressure comprises a linear approximation of the elastance function for a given volume interval.

27. The system of claim 23, further comprising:
means for selecting the relationship between the volume and the pressure from the plurality of relationships based upon a particular patient type.

28. The system of claim 23,
wherein the means for measuring the impedance comprises means for measuring a change in impedance,
wherein the means for estimating the pressure comprises means for estimating a change in pressure based on a relationship between the measured change in impedance and a change in volume of the element of the cardiovascular system and based on a relationship between the change in volume and the change in pressure.

29. The system of claim 23, further comprising:
means for selecting a combination of electrodes as the at least two electrodes based upon the element of the cardiovascular system to be measured.

30. The system of claim 23, wherein the means for measuring the impedance comprises:
means for generating a plurality of electric fields between the at least two electrodes;
means for applying the plurality of electric fields to the element of the cardiovascular system such that the combined electric field is substantially homogeneous over the element; and
means for measuring an impedance of a resultant current flow between the at least two electrodes.

31. The system of claim 23, wherein the means for measuring the impedance comprises means for measuring a complex impedance between the at least two electrodes, wherein the system further comprises means for determining a real component of the complex impedance, and wherein the means for estimating the pressure comprises means for estimating the pressure of the element of the cardiovascular system based on a relationship between the real component of the complex impedance and volume and the relationship between the volume and the pressure.

32. The system of claim 23, wherein the means for measuring the impedance comprises means for measuring a complex impedance between the at least two electrodes, and wherein the system further comprises:
means for determining a reactive component of the complex impedance; and
means for providing at least one of an indicator of hypertrophying of the element of the cardiovascular system and an indicator of myocardial tissue degradation of the element of the cardiovascular system due to ischemia based upon the reactive component of the complex impedance.

33. A non-transitory computer-readable storage medium comprising instructions that cause a processor to:
measure an impedance between at least two electrodes implanted within a cardiovascular system of a patient;
select one of a plurality of stored relationships between volume and pressure, the plurality of stored relationships comprising a relationship between volume and pressure in a vascular lumen;
select one of a plurality of stored relationships between impedance and volume based upon at least one selection criterion; and
estimate a pressure of an element of the cardiovascular system based on the relationship between the measured impedance and a volume of the element of the cardiovascular system and based on the selected relationship between the volume and the pressure, wherein the relationship between the volume and the pressure comprises an elastance function derived from empirical data comprising historical data of the patient.

34. A method comprising:
storing in a memory of an implantable medical device a plurality of relationships between volume and pressure, the plurality of relationships comprising a relationship between volume and pressure in a vascular lumen;
storing in the memory a plurality of relationships between impedance and volume;
measuring a complex impedance between at least two electrodes implanted within or proximate to a cardiovascular system of a patient;
determining a reactive component of the measured complex impedance;
enabling a control unit to select one of the stored plurality of relationships between volume and pressure and one of the stored plurality of relationships between impedance and volume based on at least one selection criterion; and
providing, by the control unit, an indication of change in size of an element of the cardiovascular system based on the reactive component of the measured complex impedance and an indication of a change in pressure in the element of the cardiovascular system based on the selected relationship between volume and pressure.

35. The method of claim 34, wherein providing the indication of change in size of the element of the cardiovascular system comprises:
providing an indication of hypertrophying of the element of the cardiovascular system based on the reactive component of the measured complex impedance.

36. The method of claim 34, wherein providing the indication of change in size of the element of the cardiovascular system comprises:

providing an indication of myocardial tissue degradation of the element of the cardiovascular system due to ischemia based on the reactive component of the measured complex impedance.

37. The method of claim 34, further comprising:
determining a real component of the measured complex impedance; and
estimating a pressure of the element of the cardiovascular system based on the real component of the measured complex impedance.

38. An implantable medical device comprising:
a memory storing a plurality of relationships between volume and pressure, the plurality of relationships comprising a relationship between volume and pressure in a vascular lumen;
the memory storing a plurality of relationships between impedance and volume;
an impedance measurement module configured to measure a complex impedance between at least two electrodes implanted within or proximate to a cardiovascular system of a patient; and
a processor configured to determine a reactive component of the measured complex impedance, and provide an indication of change in size of an element of the cardiovascular system based on the reactive component of the measured complex impedance, select one of the stored plurality of relationships between volume and pressure, select one of the stored plurality of relationships between impedance and volume based upon at least one selection criterion, and provide an indication of a change in pressure based on the change in size and the selected relationships.

39. The device of claim 38, wherein the processor is further configured to provide an indication of hypertrophying of the element of the cardiovascular system based on the reactive component of the measured complex impedance.

40. The device of claim 38, wherein the processor is further configured to provide an indication of myocardial tissue degradation of the element of the cardiovascular system due to ischemia based on the reactive component of the measured complex impedance.

41. The device of claim 38, wherein the processor is further configured to determine a real component of the measured complex impedance, and estimate a pressure of the element of the cardiovascular system based on the real component of the measured complex impedance.

* * * * *